United States Patent [19]

Davey et al.

[11] Patent Number: 5,525,709

[45] Date of Patent: Jun. 11, 1996

[54] PROCESS FOR THE PREPARATION OF CERAMIDES

[75] Inventors: Paul N. Davey, Willesborough; Brian J. Hardinge, Brabourne Lees; Christopher P. Newman, Canterbury; Clive D. Richardson, Aylesford, all of Great Britain

[73] Assignee: Unilever Patent Holdings B.V., Rotterdam, Netherlands

[21] Appl. No.: 317,908

[22] Filed: Oct. 4, 1994

[30] Foreign Application Priority Data

Oct. 4, 1993 [EP] European Pat. Off. .............. 93307882

[51] Int. Cl.$^6$ .................................................. C07C 251/00
[52] U.S. Cl. .............................. 554/68; 554/63; 554/108; 554/109; 554/110
[58] Field of Search ............................ 554/68, 63, 108, 554/109, 110

[56] References Cited

FOREIGN PATENT DOCUMENTS 0097059  12/1983  European Pat. Off. .
0500437  8/1992  European Pat. Off. .

OTHER PUBLICATIONS

N. P. Singh et al, Journal of Carbohydrate Chemistry, vol. 9, No. 5, 1990, pp. 543–559.
Chemical Abstracts, vol. 54, #5, 1960, 4404i,.
Gregory et al., Journal of Chemical Society, 1951, Letchworth GB, pp. 2453–2456.
Milan Soukup et al, Helvetica Chimica Acta., vol. 70, 1987, Basel Ch pp. 232–236
Hiroshi Kawasaki, Chemical Abstracts, vol. 54, No. 5, 10 Mar. 60, Columbus, Ohio, US, abstract No. 4404i.

Primary Examiner—José G. Dees
Assistant Examiner—Deborah D. Carr
Attorney, Agent, or Firm—Cushman Darby & Cushman

[57] ABSTRACT

The invention relates to the preparation of ceramides by a two step process involving conversion of a 2-hydroximino-3-oxo-alkanoate into a 2-alkanoylamido-3-oxo-alkanoate intermediate by acylation of the oxime and reduction of the oxime ester group to an amido group, followed by reduction of the keto and ester group of the intermediate to the 1,3 diol of the ceramide. The oxime acylation and the first reduction may be carried out consecutively or simultaneously. The first reduction is preferably a catalytic hydrogenation and the second reduction is preferably a borohydride reduction.

The invention further relates to novel 2-alkanoylamido-3-oxo-alkanoates and 2-alkanoyloximino-3-oxo-alkanoates which are useful as intermediates for conversion into ceramides.

16 Claims, No Drawings

PROCESS FOR THE PREPARATION OF CERAMIDES

The invention relates to the preparation of ceramides starting from 3-oxo-alkanoates. More particularly the invention relates to the preparation of ceramides through conversion of 2-hydroximino-3-oxo-alkanoates into 2-alkanoylamido-3-oxo-alkanoates, followed by reduction to ceramides. The invention also relates to new 2-alkanoylamido-3-oxo-alkanoates and 2-alkanoyloximino-3-oxo-alkanoates.

Ceramides are known to be important constituents of the lipid fraction of the stratum corneum of the skin, in which they are believed to perform important functions, including protection of the skin from desiccation under the influence of adverse atmospheric conditions. Therefore, ceramides have been added to various cosmetic compositions aimed at improving or restoring the protective function of the skin. Such ceramides have been obtained primarily from various animal and to a lesser extent vegetable sources.

A wealth of literature on the structure of ceramides exists, in which also their synthesis is described. Recently synthetic ceramides and ceramide analogues have been described in EP-A-0 097 059, EP-A-0 420 722 and EP-A-0 500 437. These ceramides and analogues have been synthesized from the corresponding sphingosines and dihydrosphingosines, hereinafter collectively referred to as "sphingosines". Thus, in the examples 1–4 of EP-A-0 500 437 various procedures to prepare 2-linoleylamido-1,3-octadecanediol from 2-amino-1,3-octadecanediol have been described. The sphingosines in turn are conventionally obtained by sodium borohydride reduction of 2-acetamido-3-oxo-alkanoic acid esters, whereby the keto- and ester group are reduced to hydroxy groups and simultaneously the acetyl group is removed, see EP-A-0 500 437, example 1. Various routes for obtaining sphingosines are also described by D. Shapiro in "Chemistry of Sphingolipids", Hermann, Paris (1969).

A route for obtaining 2-acetamido-3-oxo-alkanoates as precursors for sphingosines is described by G. I. Gregory and T. Malkin, J. Chem. Soc. [1951], 2453–2456, and involves oximation of methyl 3-oxo-alkanoate to the 2-hydroximino-3-oxo-alkanoates, followed by reductive acetylation of the oxime with zinc dust in a mixture of acetic acid and acetic anhydride.

The synthesis of racemic ethyl 2-acetamido-3-oxo-butyrate, through oximation of ethyl acetoacetate with sodium nitrite followed by hydrogenation over Pd/C in acetic anhydride, is described by M. Soukop et al, Helv. Chim. Acta 70 (1987) 232–236.

Synthetic ceramides have the advantage that in principle they may be obtained in high quantities, independent from the availability of natural sources, and in high purity without any microbiological contamination. However, to this end efficient ways of synthesis are needed which should preferably lead to products having as much as possible the erythro configuration found in natural ceramides.

A process for preparing ceramides from 2-hydroximino-3-oxo-alkanoates has now been found which comprises the steps of:

i—converting a 2-hydroximino-3-oxo-alkanoate of general formula I below, in which R1 is an alkyl or alkenyl group of between 10 and 23 carbon atoms, which is optionally substituted by one or more hydroxyl or alkanoyloxy groups into a 2-alkanoylamido-3-oxo-alkanoate of general formula II wherein R1 is as specified above and R3 is an alkyl or alkenyl group of between 10 and 34 carbon atoms which is optionally substituted by hydroxyl or alkanoyloxy groups;

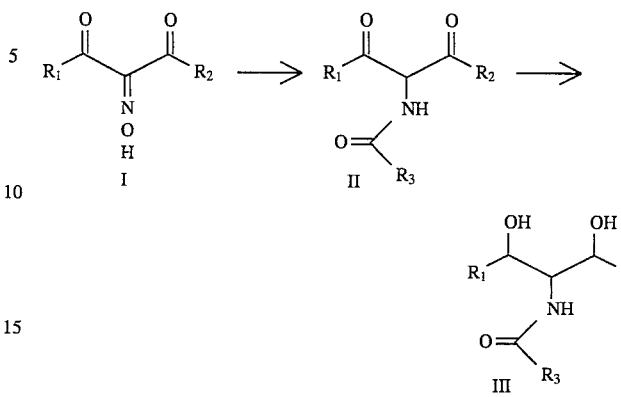

ii—reducing the 2-alkanoylamido-3-oxo-alkanoate obtained in step i to the ceramide of general formula III wherein R1 and R3 are as specified above.

Furthermore, 2-alkanoylamido-3-oxo-alkanoates of general formula II, in which R1 and R3 are as specified above, have been found which are useful intermediates enabling the efficient manufacture of ceramides with a high erythro/threo ratio.

The group R2 may be hydrogen or it may be any organic group which does not interfere with the conversion in step i and may be split off in the reduction step ii. Lower alkoxy groups, preferably of between 1 and 6 carbon atoms, are very suitable and in particular methoxy and ethoxy groups. Whatever the group R2 is in compounds I and II, for the purpose of this invention and in possible distinction to usual chemical nomenclature the compounds are consistently referred to as alkanoates.

Suitable groups R1 are e.g.:

$CH_3(CH_2)_{12}CH=CH-$ $CH_3(CH_2)_{13}CHOH-$ $CH_3(CH_2)_{15}CHOH-$ $$CH_3(CH_2)_{17}\underset{O}{CH}-$$

$CH_3(CH_2)_{21}CH(OH)-CO$

Preferably R1 is an alkyl or alkenyl group of between 10 and 23 carbon atoms optionally sybstituted by hydroxyl groups. If R1 is an alkenyl group it may be partly or completely hydrogenated during step i to the corresponding alkyl group. Particularly preferred are 2-alkanoylamido-3-oxo-alkanoates wherein R1 is $C_{13}H_{27}-$.

Suitable groups R3 are e.g.:

$CH_3(CH_2)_{22}-$ $CH_3(CH_2)_{13}CHOH-$ $CH_3(CH_2)_{21}CHOH-$ $CH_3(CH_2)_{23}CHOH-$ $CH_3(CH_2)_4CH=CHCH2CH=CH(CH_2)_7-CO-O-(CH_2)_{31}-$ $CH_3(CH_2)_4CH=CHCH2CH=CH(CH_2)_7-CO-O-(CH_2)_{29}-$ $CH_3(CH_2)_{21}CH(OH)-CO-O-(CH_2)_{29}-$

Preferably R3 is an alkyl or alkenyl group of 10–34 carbon atoms, optionally substituted by hydroxyl groups. Most preferably R3 is an alkyl or alkenyl group of 10–34 carbon atoms. Again, if R3 is an alkenyl group it may be partly or completely hydrogenated during step i to the corresponding alkyl group. Particularly preferred are 2-alkanoylamido-3-oxo-alkanoates wherein R3 is $C_{15}H_{31}$—.

Step i involves an acylation and reduction of the oxime. These reactions may be carried out consecutively, or simultaneously. The acylation may suitably be carried out by reaction of the 2-hydroximino-3-oxo-alkanoate or a derivative thereof with an acylating reagent of the general formula R3-COX wherein X is a suitable leaving group known in the art for acylating reagents.

Particularly, R3-COX may be an acyl halogenide such as an acyl chloride or it may be a symmetric or asymmetric anhydride. The reduction is carried out with a suitable reducing agent, in particular with hydrogen in the presence of a suitable hydrogenation catalyst, such as a group VIII metal on a suitable carrier. Suitable catalysts are e.g. Pt or Pd on carbon, preferably Pd/C. If these reactions are carried out simultaneously the the acylating reagent and the reducing agent (and catalyst as required) are present at the same time. In that case the acylating agent is preferably an anhydride, particularly of the formula R3—CO—O—CO—R3.

In a preferred embodiment the 2-hydroximino-3-oxo-alkanoate I is first acylated to form a 2-alkanoyloximino-3-oxo-alkanoate of general formula Ia

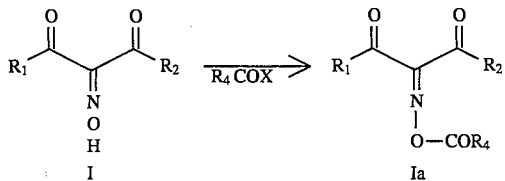

wherein R4 is an alkyl group of between 1 and 34 carbon atoms, e.g. with an acylating reagent of the general formula R4-COX, wherein X has the meaning specified above. Preferably R4 is a lower alkyl group of 1–4 carbon atoms. Most preferably the 2-hydroximino-3-oxo-alkanoate is acetylated to 2-acetoximino-3-oxo-alkanoate (R4= methyl) with acetyl chloride or acetic acid anhydride or another suitable acetylating agent. Subsequently, the compound Ia is reacted with R3-COX, preferably R3—CO—O—CO—R3, and hydrogen in the presence of a hydrogenation catalyst.

Thus, 2-alkanoyloximino-3-oxo-alkanoates of general formula Ia in which R4 has the meaning given above have been found which are useful intermediates enabling the efficient manufacture of ceramides.

In another preferred embodiment the 2-hydroximino-3-oxo-alkanoate is directly reacted simultaneously with the anhydride R3—CO—O—CO—R3 and hydrogen in the presence of a hydrogenation catalyst.

Step ii involves a reduction in compound II of both carbonyl groups originally derived from compound I to hydroxy groups. Hydride reducing agents, particularly borohydrides are preferred for this purpose, especially sodium borohydride.

Sodium borohydride reduction of 2-acetylamido-3-oxo-alkanoates has been described in EP-A-0 500 437, in which case the amido group is reduced as well, resulting in removal of the acetyl group and formation of the amine, which thereafter has to be acylated to obtain the desired ceramide.

However, unlike the 2-acetylamido-3-oxo-alkanoates of the prior art, the 2-alkanoylamido-3-oxo-alkanoates according to general formula II have been found to retain the amido group while being reduced with borohydride. Thus the desired ceramides are obtained directly without the need for further acylation.

If R1 and/or R3 are caused to contain hydroxy groups in the chain, these may be converted into double bonds by methods known in the art after completion of step i, thus preventing undesired hydrogenation of such double bonds in step i. Alternatively a hydroxy group may be esterified with a an alkanoic acid after completion of step ii, to obtain any of the esterified groups R1 and/or R3.

The 2-hydroximino-3-oxo-alkanoate starting materials for the process may be obtained according to methods known in the art, particularly as described by Gregory & Malkin or analogous to the procedure described by Soukop (vide supra). Both methods involve nitrosation of a suitable 3-oxo-alkanoate, which in turn may be obtained according to methods known in the art, e.g. by reaction of R1—CO—CH3 with dialkyl carbonate or by reaction of R1—COCl with dialkyl malonate or alkyl acetoacetate, all in the presence of a suitable base.

The anhydrides R3—CO—O—CO—R3 may be prepared according to procedures known in the art, e.g. according to D. Holde, J. Ripper and F. Zadek, Ber. 57B, 103 (1924).

The ceramides are obtained as racemic mixtures and generally have an erythro/threo ratio of 50:50 or higher, particularly 70:30 or higher.

The ceramides obtained by the process according to the invention can be used in cosmetic and dermo-pharmaceutical compositions as is known in the art for such compounds and be combined with various raw materials known in the art for such compositions, vide EP-A-0 500 437 and EP-A-0 420 722. On dispersion in water they have the ability to form multilayered vesicular structures which improve the desirable properties of the cosmetic compositions.

The invention is illustrated by the following examples.

EXAMPLE: 1

Preparation of 2-hexadecanoylamido-1,3-hexadecanediol

Stage 1: Preparation of the keto oxime ester (KOE)

Methyl 3-oxo-hexadecanoate (23.67 g, 0.083 moles, mp 39° C.) was charged to a 250 ml three-necked round bottomed flask fitted with a stirrer, dropping funnel, thermometer, nitrogen inlet and condenser. Methanol (79.1 g, 2.47 moles) and glacial acetic acid (14.5 g, 0.24 moles) were added and the resulting solution was stirred at 25° C. Aqueous sodium nitrite solution (12.0 g, 0.175 moles) in water (18.3 g) was added to this stirred solution over 1 hour, with external cooling (if necessary) to keep the temperature below 30° C. A white precipitate was produced at first which slowly dissolved later. Post addition stir was continued for 18 hours at 25° C. After this time a clear, green/yellow solution was produced which was quenched slowly into water (150 g) and stirred for 1 hour. The resultant solid product was extracted several times with warm (45° C.) cyclohexane and this solution of crude Keto Oxime Ester I (26 g) in cyclohexane was dried and thereafter used for the next stage.

Stage 2: Preparation of the keto oxime acetate ester (KOAcE, Ia)

Keto oxime ester (KOE) (60.0 g, 0.19 moles) dissolved in cyclohexane (195 g) obtained in Stage 1, was charged to a 500 ml three-necked flask, fitted with a stirrer, thermometer and reflux condenser. Sodium acetate (0.5 g) was added followed by acetic anhydride (40.0 g, 0.39 moles). This mixture was stirred at 50° C. for 1 hour before cooling to room temperature. The reaction mixture was washed once with water and the solution of crude keto oxime acetate ester (KOAcE) Ia in cyclohexane, still containing some acetic acid, was then used in the next stage.

Stage 3: Hydrogenation/Amidation to keto amide ester (KAE, II)

Cyclohexane (780.0 g) was charged to a 6 liter reaction vessel fitted with a mechanical stirrer, thermometer, water condenser and gas inlet and outlet tubes. Palladium (5% on charcoal, 4.0 g) was added and stirred, while the apparatus was purged with nitrogen. KOAcE (150.0 g, 0.423 moles, in 500 g of cyclohexane, obtained in Stage 2) was then added followed by a slurry of palmitic anhydride (250.0 g, 0.505 moles) in cyclohexane (1460 g). This suspension was stirred at room temperature and further purged with nitrogen, then purged with hydrogen before closing the outlet tap and closing the reactor under an atmosphere of hydrogen. Hydrogen gas was continued to be passed into the reactor via a gas meter till there was no further uptake of gas (29.41 of hydrogen were measured in 7 hours). The reaction mixture was then heated, with stirring, to 40° C. to dissolve a white solid present, and this hot solution was filtered through a celite bed (80.0 g) to remove the catalyst. On cooling the filtrate, a white solid of the keto amide ester (KAE) crystallised out, was filtered off, washed with cyclohexane and dried in a vacuum oven. The yield of KAE was 89.0 g (40.0% chemical yield based on KOAcE used).

Stage 4: Reduction to Ceramide (III)

Pure keto amide ester (KAE) (2.0 g, $3.7 \times 10^{-3}$ moles, obtained in Stage 3) was placed in a 250 ml three necked round bottomed flask, fitted with a mechanical stirrer, thermometer, dropping funnel and condenser. Cyclohexane (50.0 g) was added and the mixture warmed to 40° C. to dissolve the keto ester amide, this temperature was maintained during the addition of a solution containing sodium borohydride (0.62 g) in isopropanol (30 ml) which was added over a 30 minute period. During the addition the temperature increased from 41° C. to 45° C. On completion of the addition the cloudy suspension was stirred at 45° C. to 50° C. for two hours, then refluxed at 70° C. for a further two hours and then allowed to cool to room temperature and left to stand overnight. The resultant clear, colourless reaction mixture which contained small amounts of undissolved solid was quenched into water (100 ml). This resulted in the formation of two layers, an upper white emulsion layer and a clear lower layer (pH 8–9). The lower aqueous layer was separated off and discarded, 20 ml of isopropanol was added to the organic layer which resulted in the formation of a colourless homogeneous solution, the solvent was removed by rotary evaporation leaving the ceramide as a white solid (1.9 g, erythro/threo: 70/30 by nmr).

The solid was dissolved in and recrystallised from isopropanol and dried in vacuo. This yielded 1.5 g, i.e., 79% on KAE. The ceramide consisted of a mixture of the two isomers erythro (80%) and threo (20%). The mother liquor yielded 0.4 g solid, erythro/threo 40/60.

Preparation of Palmitic Anhydride

Palmitic acid (512.04 g, 2.00 moles) and acetic anhydride (204.05 g, 2.00 moles) were charged to a two liter reaction flask fitted with an overhead stirrer, thermometer, condenser and nitrogen inlet. The mixture was heated gently with stirring to allow the solid palmitic acid to melt (61° C. to 64° C.). Heating was continued until the reflux temperature had been reached (147° C.), this temperature was maintained for a period of one hour. The resultant mixture was cooled to room temperature to allow a light yellow solid to form, this was slurried in cyclohexane (100 ml), filtered and recrystallised from petroleum ether 60–80. The recrystallised wet solid was placed in a vacuum oven at 40° C. until dry of residual acetic acid. The resultant white powdery solid was stored under vacuum in the presence of silica gel. The yield of palmitic anhydride was 458.49 g which represented a 92.8% chemical yield.

EXAMPLE 2

Methyl 3-oxo-hexadecanoate was treated with sodium nitrite as described in EXAMPLE 1 and the resulting keto oxime ester further converted as described further down below or, alternatively, the keto oxime ester could be obtained as described directly below:

Methyl 3-oxo-hexadecanoate (500 g, 1.76 moles mp. 39° C.) was charged to a 5l three-necked round bottomed flask fitted with a stirrer, dropping funnel, thermometer and condenser. Methanol (1250.0 g, 40.32 moles) and acetic acid, glacial (306.0 g, 5.1 moles) were added and the resulting solution was stirred at 40° C. Sodium nitrite (253.5 g, 3.67 moles) in water (386.6 g) was added to this stirred solution over 45 minutes, with external cooling (if necessary) to control the exotherm and keep the temperature below 45° C., followed by a post addition stir of 1 hour at 40° C.–45° C. After this time a clear, green/yellow solution was produced which was quenched slowly into water (1250 g) and hexane (702 g) and stirred for 15 minutes at 40° C. The layers were separated, and the lower aqueous layer (2116.0 g) discarded. The top organic layer was washed with water (948.0 g) and methanol (100 g) at 40° C. and the lower aqueous layer discarded. The upper organic layer as a cloudy, yellow solution, was filtered to give a clear solution which was evaporated to dryness to give 506.2 g of the crude KOE as a pale yellow solid (yield=101.2% m/m or 91.9% chemical based on the KE used).

Palmitic acid (495.6 g, 1.936 moles) and acetic anhydride (197.5 g, 1.936 moles) were placed in a 1l three necked round-bottomed flask, fitted with a thermometer, stirrer and reflux condenser. This mixture was stirred at 145°–148° C. for 1 hour and then cooled to 110° C. The apparatus was then set up for distillation and the volatile components (acetic acid and excess acetic anhydride) were removed from the reactor a pot temperature of 100° C. and under reduced pressure. The molten residue of palmitic anhydride (486 g, 0.983 moles) was then used without further purification.

Keto oxime ester (crude, 300 g, 0.96 moles) in cyclohexane (2.5l) was charged to a 5l reaction vessel fitted with a mechanical stirrer, thermometer, and gas inlet and outlet tubes. Palladium (5% on charcoal, 6.0 g) and palmitic anhydride (486.0 g, 0.983 moles, prepared as above) were added and the apparatus purged with nitrogen while maintaining the temperature at 20°–25° C. The apparatus was then purged with hydrogen before closing the outlet tap and closing the reactor under an atmosphere of hydrogen. Hydrogen gas was then continued to be passed into the reactor via a gas meter till there was no further uptake of gas (59.8l of hydrogen were measured in 17.5 hours) and the temperature during this addition gradually increased to 40° C. at the end of the reaction. The reaction mixture was filtered at 40° C. through a Celite bed to remove the catalyst and the filtrate allowed to cool. On cooling, the white precipitate formed was filtered off, washed with a little cyclohexane and dried in a vacuum oven. The yield of KAE 179.0 g (60% w/w yield, 35% chemical yield based on KOE used). The material could be further purified by recrystallization from hexane.

The keto amide ester KAE (100 g, 0.186 moles) and 2-propanol (300 g) were charged to a 1000 ml round-bottomed flask fitted with a thermometer, stirrer and reflux condenser and heated to 55° C. whereby a clear homogeneous solution was obtained. Solid sodium borohydride (7.6 g, 186 moles) was added over 30 minutes. The reaction was slightly exothermic. The cloudy suspension obtained was further stirred for another 30 minutes, thereafter cooled to 40° C. and acetone (10.79, 0.186 moles) was added and stirring continued for another 30 minutes to destroy any excess hydride. Subsequently the reaction mixture was cooled to room temperature and quenched in water (700 g). The cloudy white emulsion was heated to 70° C. which led to the formation of two distinct clear layers. These were separated and on cooling to room temperature the top layer formed a wet white solid (153 g). The crude solid was evaporated to dryness on a rotary evaporator at 90° C. to give 111,4 dry solid which was recristalized from 250 g 2-propanol. Thus 2-hexadecanoylamido-1,3-hexadecanediol was obtained as a white fluffy powder (74.9 g, 78.9% yield on KAE used). The product was pure as tested by NMR.

EXAMPLE 3

Preparation of 2-(16'-hydroxy-hexadecanoylamido)-1,3-hexadecanediol

This compound was prepared according to the procedure of EXAMPLE 2 using the diacetate of 16-hydroxy-palmitic anhydride. The anhydride diester was prepared according to the above described procedure from 16-hydroxy-palmitic acid and acetic anhydride. The sodium borohydride reduction in the last step also removed the acetyl group from the 16'-hydroxyl group. This hydroxyl group may be esterified with a long-chain alkanoic acid, preferably after protection of the 1,3-diol moiety as a cyclic acetal or ketal as known in the art.

EXAMPLE 4

Preparation of
2-hexadecanoylamido-1,3,11,12,18-octadecanepentaol
and
2-hexadecanoylamido-1,3,18-octadec-11-enetriol Methyl 11,12,18-trihydroxy-3-oxo-octadecanoate was prepared by treating 9,10,16-trihydroxy-palmitic acid (aleuritic acid) with acetyl chloride to protect the three hydroxyl groups. The acid was then converted into its acid chloride which was condensed with methyl acetoacetate followed by mild alkaline hydrolysis. Thus, the ketoester methyl 11,12, 18-trihydroxy-3-oxo-octadecanoate, with the three hydroxyl groups protected by acetyl groups, was obtained. This compound was used as the starting material in the process according to EXAMPLE 1 which led to the desired pentaol. The vicinal diol group in this molecule may be converted into a double bond by standard methods known in the art thus leading to 2-hexadecanoylamido-1,3,18-octadec-11-enetriol.

We claim:
1. Process for preparing ceramides from 2-hydroximino-3-oxo-alkanoates characterized in that it comprises the steps of:
i—converting a 2-hydroximino-3-oxo-alkanoate of general formula I below, in which R1 is an alkyl or alkenyl group of between 10 and 23 carbon atoms, which is optionally substituted by hydroxyl or alkanoyloxy groups, and in which R2 is hydrogen or is an organic group which does not interfere with the conversion in step i and may be split off in the reduction step ii, into a 2-alkanoylamido-3-oxo-alkanoate of general formula II wherein R1 and R2 are as specified above and R3 is an alkyl or alkenyl group of between 10 and 34 carbon atoms which is optionally substituted by hydroxyl or alkanoyloxy groups;

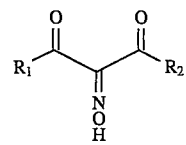

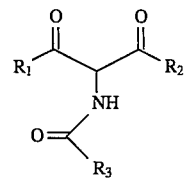

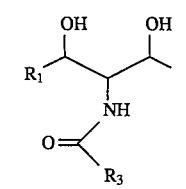

ii—reducing the 2-alkanoylamido-3-oxo-alkanoate obtained in step i to the ceramide of general formula III wherein R1 and R3 are as specified above.

2. Process according to claim 1 wherein R2 is a lower alkoxy group.
3. Process according to claim 1 wherein R1 is an alkyl or alkenyl group of between 10 and 23 carbon atoms, optionally substituted by hydroxyl groups.
4. Process according to claim 3 wherein R3 is an alkyl or alkenyl group of 10–34 carbon atoms, optionally substituted by hydroxyl groups.
5. Process according to claims 1 wherein the 2-hydroximino-3-oxo-alkanoate is first converted into a 2-alkanoyloximino-3-oxo-alkanoate of general formula Ia wherein R4 is an alkyl group of between 1 and 34 carbon atoms.
6. Process according to claim 5 wherein R4 is an alkyl group of between 1 and 4 carbon atoms.
7. Process according to claim 6 wherein step i involves hydrogenation in the presence of a group VIII hydrogenation catalyst.
8. Process according to claim 7 wherein the hydrogenation is carried out simultaneously with acylation with an anhydride R3—CO—O—CO—R3.
9. Process according to claims 8 wherein the 2-alkanoylamido-3-oxo-alkanoate is reduced to the ceramide with a hydride reducing agent.
10. Process according to claim 9 wherein the hydride reducing agent is a borohydride.
11. 2-alkanoylamido-3-oxo-alkanoates according to general formula II

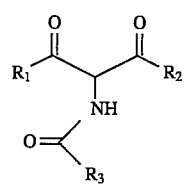

wherein R1 is an alkyl or alkenyl group of between 10 and 23 carbon atoms, which is optionally substituted by hydroxyl or alkanoyloxy groups, R2 is hydrogen or is an organic group which does not interfere with the conversion in step i and may be split off in the reduction step ii and R3 is an alkyl or alkenyl group of between 10 and 34 carbon atoms which is substituted by hydroxyl or alkanoyloxy groups 12. 2-alkanoylamido-3-oxo-alkanoates according to claim 11 wherein R2 is a lower alkoxy group.

13. 2-alkanoylamido-3-oxo-alkanoates according to claim 11 wherein R1 is an alkyl or alkenyl group of between 10 and 23 carbon atoms, optionally substituted by hydroxyl groups.

14. 2-alkanoylamido-3-oxo-alkanoates according to claim 11 wherein R3 is an alkyl or alkenyl group of 10–34 carbon atoms, substituted by hydroxyl groups 15. 2-alkanoyloximino-3-oxo-alkanoates of general formula Ia wherein R4 is an alkyl group of between 1 and 34 carbon atoms and R1 is an alkyl or alkenyl group of between 10 and 23 carbon atoms, which is optionally substituted by hydroxyl or alkanoyloxy groups, R2 is hydrogen or is an organic group:

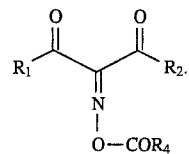

16. 2-alkanoyloximino-3-oxo-alkanoates according to claim 15 wherein R4 is an alkyl group of between 1 and 4 carbon atoms.

* * * * *